United States Patent [19]
Campbell et al.

[11] Patent Number: 6,090,035
[45] Date of Patent: Jul. 18, 2000

[54] STENT LOADING ASSEMBLY FOR A SELF-EXPANDING STENT

[75] Inventors: Thomas H. Campbell, Redwood City; Robert T. Chang, Belmont, both of Calif.

[73] Assignee: IsoStent, Inc., Belmont, Calif.

[21] Appl. No.: 09/273,072

[22] Filed: Mar. 19, 1999

[51] Int. Cl.[7] .............................. A61M 36/00; A61N 5/00
[52] U.S. Cl. .................................................... 600/7; 600/3
[58] Field of Search ................................... 600/1, 2, 3, 4, 600/5, 6, 7, 8; 606/194, 198, 108

[56] References Cited

U.S. PATENT DOCUMENTS

| | | |
|---|---|---|
| 4,768,507 | 9/1988 | Fischell et al. . |
| 5,026,377 | 6/1991 | Burton et al. . |
| 5,437,083 | 8/1995 | Williams et al. . |
| 5,605,530 | 2/1997 | Fischell et al. . |
| 5,626,604 | 5/1997 | Cottone, Jr. . |
| 5,630,830 | 5/1997 | Verbeek . |
| 5,672,169 | 9/1997 | Verbeek . |
| 5,693,066 | 12/1997 | Rupp et al. . |
| 5,725,519 | 3/1998 | Penner et al. . |
| 5,738,674 | 4/1998 | Williams et al. . |
| 5,746,764 | 5/1998 | Green et al. . |

FOREIGN PATENT DOCUMENTS

| | | |
|---|---|---|
| 0826346A1 | 3/1998 | European Pat. Off. . |
| WO 98/19633 | 5/1998 | WIPO . |
| WO99/59503 | 11/1999 | WIPO . |

*Primary Examiner*—Max Hindenburg
*Assistant Examiner*—Brian Szmal
*Attorney, Agent, or Firm*—Beyer Weaver & Thomas, LLP

[57] ABSTRACT

A stent loading apparatus for loading a self-expanding radioactive stent into a bore of a deployment device in a compressed condition including a storage device defining an elongated first passage formed and dimensioned for sliding receipt of the stent therein. The first passage extends through the storage device and terminates at a stent transfer opening of a proximal coupling end thereof. A radiation shield defines an elongated second passage which terminates at a distal opening of a distal coupling end thereof. The distal coupling end of the radiation shield and the proximal coupling end of the storage device cooperate to align the distal opening of the shield in receiving communication with the stent transfer opening of the storage device. The second passage of the shield is formed and dimensioned for receipt of the deployment device therein in a manner positioning a mouth of the deployment device bore substantially adjacent the stent transfer opening of the storage device. Upon urging of the stent in a direction toward the shield, the radioactive stent may be slideably transferred from the first passage and into the mouth of the bore for retainment therein in the compressed condition.

42 Claims, 10 Drawing Sheets

STENT LOADING ASSEMBLY FOR A SELF-EXPANDING STENT

TECHNICAL FIELD

The present invention relates, generally, to intravascular stents and, more particularly, to stent loading assemblies for self-expanding radioactive stents.

BACKGROUND ART

Percutaneous Transluminal Angioplasty (PTA) is a medical procedure for widening a stenosis or constriction of a bodily passage. The most common application is to widen the passage of a blood vessel, such as an artery, which has been constricted by the build-up of cholesterol fats or atherosclerotic plaque. When this medical procedure is applied to a coronary artery, it is referred to as Percutaneous Transluminal Coronary Angioplasty (PTCA).

Typically, a tip mounted balloon of a balloon catheter is advanced over a guidewire to the stenosis. Once the balloon catheter is properly position, the balloon is inflated to compress the plaque against the vessel walls and widen the stenosis. Problems occur, however, when the dilatation of the occlusion forms fissures, flaps and/or dissections which may ultimately cause reclosure or restenosis of the vessel.

To maintain vessel patency and/or strengthen the area undergoing angioplasty or other treatment, an intravascular prosthesis may be employed. These devices are usually introduced percutaneously, transported transluminally and positioned at a desired location within the widened stenosis of the patient. Once properly deployed, the implanted intravascular prosthesis essentially functions as a permanent scaffold for the widened stenosis to reduce the chance of restenosis.

One form of an intravascular prosthesis is a self-expanding stent device which is capable of self-expansion to its proper implantation size after deployment at the site of the stenosis. Usually, these stent devices either self-expand due to exposure to environmental factors (usually the application of body heat), and/or are radially constrained in a compressed condition by a deployment device until released. In the latter design, upon proper positioning and removal of the peripheral constraint, such as a sheath, the self-expanding stent reverts to its expanded state. Self-expanding stents of this nature are generally composed of shape memory alloys or the like such as nitinol which are configured to have a transition temperature just below the normal body temperature. Typical of these self-expanding stents is disclosed in U.S. Pat. No. 4,655,771.

More recently, however, these conventional self-expanding stents (as well as balloon expandable stents) have been embedded or implanted with radioisotopes which they emit predictable amounts of radiation into the widened vessel and immediate surrounding area. It has been found that the proper dosages of radiation reduces tissue regrowth, an effect which is highly beneficial in preventing restenosis of the vessel. Such radioisotope stents are disclosed in U.S. Pat. Nos.: 5,059,166 and 5,176,617, incorporated by reference herein in their entirety.

Although these radioactive stents only emit relatively low levels of radiation, direct contact with the stent by physicians, laboratory technicians, and other personnel should be avoided. As a result, special handling and storage protocols for these radioactive stents must be exercised to minimize radiation exposure. For example, shielding devices have been developed to enable the safe transportation and handling of these radioactive stents and/or the associated stent delivery catheters. Such shield devices are disclosed in U.S. Pat. No. 5,605,530, entitled "System for Safe Implantation of Radioisotope Stents", which is incorporated by reference in its entirety.

Similarly, to transport and deploy these self-expanding radioactive stents, special deployment catheters are applied which have distal tubes containing the compressed stents therein. Once the distal tube is properly advanced and situated at the widened stenosis or the like, the stent is forced from the tube whereupon the stent self-expands to the expanded state. Examples of these deployment devices may be found in U.S. Pat. Nos.: 5,026,377; 4,768,507 and 4,732,152.

The primary problem associated with these deployment devices, however, is that the self-expanding stents (both radioactive and non-radioactive stents) must be compressed before being installed in the distal tube of the deployment device. In some instances, on-site manual compression may be performed by the physician in the catheter laboratory. This process enables the physician to "feel" the compression and to determine the load quality in the delivery tube. The proper compression technique for a self-expanding stent, however, is extremely difficult to perform, and is generally acquired only through substantial practice and experience. A variety of subjective conditions, such as too great or too little compression pressure, may affect the structural integrity and irreparably damage stent. Damage may also occur during loading of the compressed stent into the delivery tube. Moreover, when radioactive stents are applied, direct handling thereof by the physician should generally be avoided altogether.

More preferably, these radioactive self-expanding stents are precompressed for storage in associated deployment devices or catheters at the time of production by the manufacturer. While this loading technique more uniformly controls the loading quality of the compressed stents, a large inventory of self-expanding stent-bearing deployment catheters must be maintained to accommodate the variety of stent types, diameters and stent lengths for each type of delivery catheter. Thus, maintaining such an inventory is not only difficult, but can be very expensive as well.

Moreover, the storage of radioactive stents in these catheters tends to be problematic since the shelf-life for the radioactive stent is substantially different from that of the deployment catheter, depending upon the isotope half-life (e.g., a beta or gamma isotope). For example, the shelf-life for a radioactive stent may range from about 3 days to about 100 days; while that of the deployment device may be about 3 years. This disparity again increases the difficulty of inventory maintenance.

Therefore, it would be highly desirable to uniformly load a self-expanding radioactive stent into deployment device on-site at the catheter laboratory or the like, without requiring the physician, laboratory technician or other personnel to directly handle and contact the radioactive stent.

DISCLOSURE OF INVENTION

Accordingly, a stent loading apparatus is provided for loading a self-expanding radioactive stent into a bore portion of a deployment device which is configured for sliding receipt and retainment of the radioactive stent therein in a compressed condition. The loading apparatus includes a storage device defining an elongated first passage formed and dimensioned for sliding receipt of the radioactive stent in the compressed condition. The first passage, extending longitudinally through the storage device, terminates at a stent transfer opening of a proximal coupling end thereof. A radiation shield defines an elongated second passage which terminates at a distal opening of a distal coupling end thereof. The distal coupling end of the radiation shield and the proximal coupling end of the storage device cooperate to align the distal opening of the radiation shield in receiving communication with the stent transfer opening of the storage device. The second passage of the radiation shield is formed and dimensioned for receipt of the deployment device therein in a manner positioning a mouth portion of the deployment device bore portion substantially adjacent the stent transfer opening of the storage device. Upon urging of the radioactive stent in a direction toward the radiation shield, the radioactive stent may be slideably transferred from the first passage and into the mouth portion of the bore portion for retainment therein in the compressed condition.

In one embodiment, the distal coupling end of the radiation shield and the proximal coupling end of the storage device cooperate to axially align the distal opening of the radiation shield with the stent transfer opening of the storage device. The radiation shield distal coupling end includes an elongated proboscis which defines the distal opening and upon which the second passage extends longitudinally therethrough. The storage device proximal end defines a receiving port formed and dimensioned for sliding receipt of the proboscis therein during aligned coupling between the distal coupling end and the proximal coupling end.

In another configuration, the stent transfer opening into first passage of the storage device further terminates at a nipple portion. This extension tapers inwardly and extends into the receiving port. The nipple portion has a proximal end adapted to extend into the distal opening of the proboscis during the aligned coupling such that the stent transfer opening of the storage device is positioned inside the distal opening of the radiation shield.

In yet another embodiment, a shrink-wrap material is shrunk substantially around the collective periphery of the storage device and the radiation shield which stably couples the storage device and the radiation shield together.

In another stent loading apparatus embodiment, a storage device defines an elongated first passage which is formed and dimensioned for sliding receipt of the stent in the compressed condition. The first passage extends longitudinally through the storage device from an access opening to an opposite stent transfer opening. A shield device is further provided which includes an elongated second passage terminating at a distal opening. The second passage is formed and dimensioned for receipt of the deployment device therein in a manner positioning a mouth portion of the deployment device bore portion proximate the distal opening of the second passage. A coupling device releasably couples the shield device to the storage device to align the distal opening of the shield device in receiving communication with the stent transfer opening of the storage device. The stent loading apparatus further includes an elongated mandrel configured to slideably extend through the access opening into the first passage and into abutting contact with the stent in the compressed condition. Upon further movement toward the second passage, the mandrel urges the stent from the first passage of the storage device to the second passage of the shield device and into the mouth portion of the bore portion for retainment therein in the compressed condition.

In one embodiment, the mandrel includes a pushrod having a distal shoulder portion adapted to abut a distal end of the compressed stent, and a support portion extending from the shoulder portion of the pushrod. This support structure is adapted to extend into the compressed stent, while it is maintained in the compressed condition, for radial support during transfer from the first passage and into the bore portion of the deployment device. The support portion includes an insert end which is configured to extend past the proximal end of the stent when mandrel distal shoulder portion abuts the distal end of the compressed stent. This insert end is further sized to extend into the mouth portion of the bore portion of the deployment device during transfer of the compressed stent into the bore portion of the deployment device.

In still another construction, an actuation device in the form of a syringe assembly is coupled to the mandrel for selective movement between a first position and a second position. In the first position, the support portion of the mandrel is placed in the stent while the stent is maintained in the compressed condition in the storage device. In the second position, the support portion and the compressed stent are urged simultaneously as a unit into the bore portion of the deployment device in the shield device.

The syringe assembly includes a contact end adapted to extend into the access opening of the storage device to enable aligned movement of the mandrel to the first position. The contact end is tapered inwardly and adapted to be press-fit into the access opening of the storage device.

In still another invention, a method for loading a self-expanding stent, in a compressed condition, into a bore portion of a deployment device is provided. The method includes: inserting the stent longitudinally into an elongated first passage of a storage device configured for sliding receipt of the stent therein in the compressed condition; and releasably coupling a shield device to the storage device in a manner aligning a distal opening of an elongated second passage extending through the shield device with a stent transfer opening of the first passage of the storage device. The method further includes the events of positioning the deployment device in the elongated second passage such that a mouth portion into bore portion of the deployment device is positioned proximate the distal opening of the second passage; and urging the compressed stent in the first passage of the storage device from the stent transfer opening through the distal opening into the second passage, and into the mouth portion of the bore portion for retainment therein in the compressed condition.

BRIEF DESCRIPTION OF THE DRAWING

The assembly of the present invention has other objects and features of advantage which will be more readily apparent from the following description of the best mode of carrying out the invention and the appended claims, when taken in conjunction with the accompanying drawing, in which:

BEST MODE OF CARRYING OUT THE INVENTION

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Figure 1:
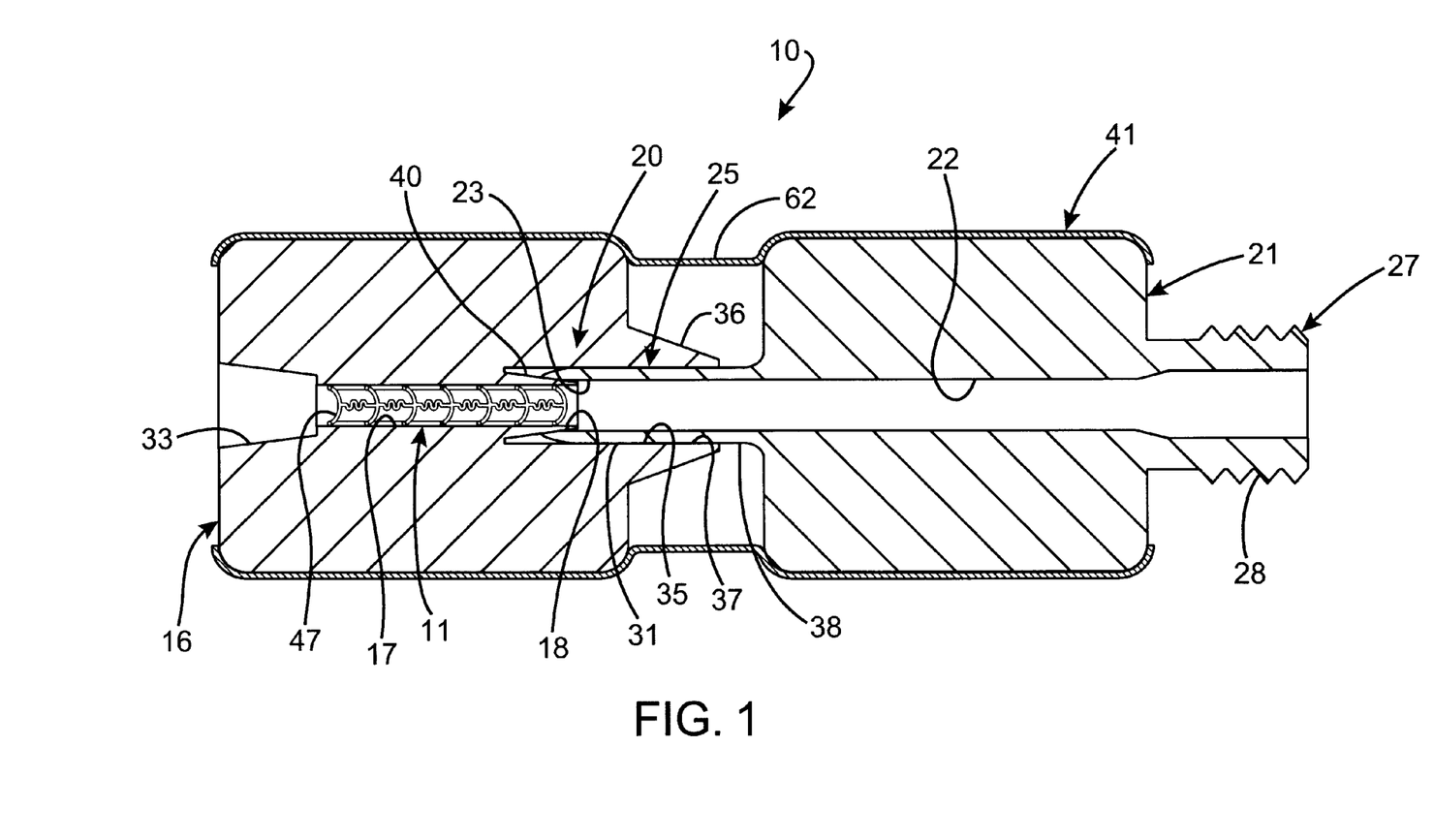
FIG. 1 is a fragmentary, side elevation view, in cross-section, of stent loading apparatus constructed in accordance with the present invention showing the coupling between a storage device and a radiation shield device.
Figure 2:
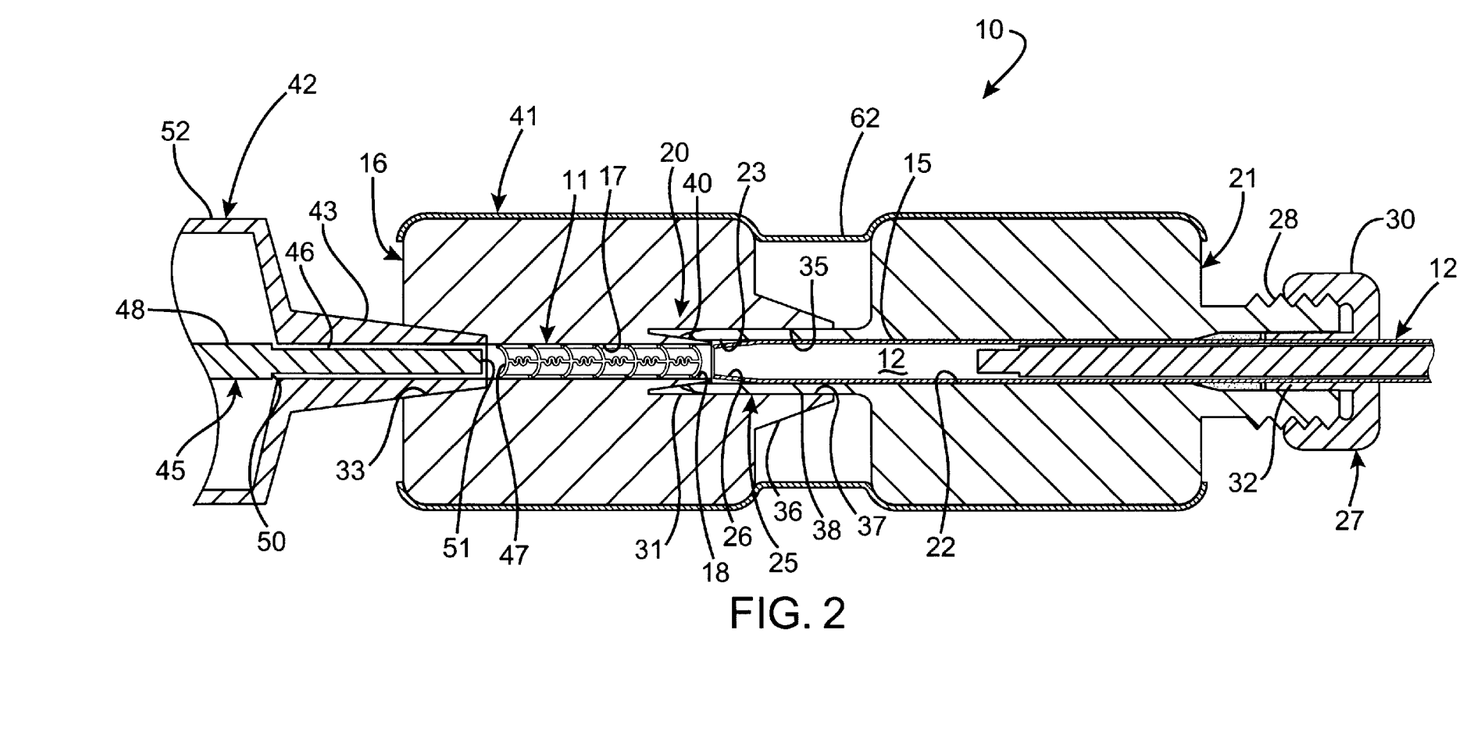
FIG. 2 is a fragmentary, side elevation view, in cross-section, of stent loading apparatus of FIG. 1 having an actuation device and a deployment catheter mounted thereto.

Attention is now directed to FIGS. 1 and 2, where a stent loading apparatus, generally designated 10, is provided for loading a self-expanding stent 11 into a bore portion 12 of a deployment device 13. Briefly, the deployment device is provided by a catheter or the like having an open ended distal tube or sheath 15 which is configured for sliding receipt and retainment of the stent 11 therein in a compressed or folded condition. The stent loading apparatus 10 of the present invention includes a storage device, generally designated 16, defining an elongated first passage 17 formed and dimensioned for sliding receipt and retainment of the radioactive stent in the compressed condition. The first passage 17, which extends through the storage device 16, terminates at a stent transfer opening 18 of a proximal coupling end 20 thereof. In accordance with the stent loading apparatus of the present invention, a radiation shield, generally designated 21, is further provided which includes an elongated second passage 22 which terminates at a distal opening 23 of a distal coupling end 25 thereof. The distal coupling end 25 of the radiation shield device 21 and the proximal coupling end 20 of the storage device 16 cooperate to align the distal opening 23 of the radiation shield device 21 in receiving communication with the stent transfer opening of the storage device 16. The second passage 22 of the radiation shield device 21 is formed and dimensioned for receipt of the deployment device 13 therein in a manner positioning a mouth portion 26 of the deployment device bore portion 12 substantially adjacent the stent transfer opening 18 of the storage device 16. Upon urging of the radioactive stent 11 in a direction toward the radiation shield device 21, the stent 11 may be slideably transferred from the first passage 17 of the storage device 16 into the mouth 26 of the bore portion 12 of the deployment device for retainment therein while still maintained in the compressed condition.

Accordingly, a stent loading apparatus is provided for a self-expanding stent which enables on-site loading of the stent into a deployment device without requiring direct contact with the stent by the physician or laboratory personnel. This arrangement, thus, is extremely suitable for radioisotope stents since direct contact with the stent may be avoided during loading. Moreover, the need to carry a large inventory of self-expanding stent-bearing deployment catheters is eliminated, as well as eliminating the problems caused by the disparities in the shelf-lives of the componentry. Additionally, the uniformity and quality of the pre-compression and loading may improved to substantially match that of the precompressed stent-bearing deployment catheters.

Briefly, while the present invention is particularly suitable for self-expanding radioactive stents, it will be appreciated that this application may be applied to non-radioactive stents as well. Further, it will be understood that the term "compressed condition" applies to any radial compression, folding and/or other technique conventionally applied to a self-expanding stents for delivery and transfer.

In the preferred embodiment, the storage device 16 is adapted to releasably couple to a radiation shield device 21 of the type employed to transport and deliver a stent loaded deployment device for self-expanding stents. These radiation shield devices may be provided by the single piece type disclosed in U.S Pat. No. 5,605,530 above-discussed, or may be provided by the two-piece clam shell type which is the subject of U.S. patent application Ser. No. 09/236,770, filed Jan. 25, 1999, and incorporated by reference in its entirety. Briefly, these radiation shield devices 21 are generally cylindrical in shape, and are composed of materials capable of substantially preventing exposure to radiation emitted by the radioisotope stent carried therein. Such materials typically include moldable plastics such as acrylic or a polycarbonate.

As best viewed in FIGS. 1 and 2, the proximal end of the radiation shield device 21 is configured to accommodate a Tuohy-Borst fitting 27 having a threaded section 28 and a nut 30. At the opposite distal coupling end 25 is a proboscis 31 which further defines the distal opening 23 into the second passage 22. Preferably, the second passage 22 is substantially linear, and extends from the Tuohy-Borst fitting 27 to the distal end of the proboscis 31. This passage is formed and dimensioned to slideably receive the elongated deployment device 13 therein which is inserted through the Tuohy-Borst fitting 27 to a position placing the mouth portion 26 into the bore 12 of sheath 15 proximate the distal opening 23 of the second passage 22.

Upon proper positioning of the deployment device, the nut 30 threaded onto the threaded section 28 is tightened which in turn inwardly deforms a deformable neck 32 of the fitting 27. Consequently, the deployment device is frictionally retain in the second passage 22 of the radiation shield to prevent it from inadvertently sliding off the deployment device. Thus, accidental exposure to the radiation emanating from the radioisotope stent is substantially reduced.

Similar to the radiation shield device, the storage device 16 is substantially cylindrical, and is preferably composed of moldable plastic such as acrylic or a polycarbonate. It will be appreciated that both the radiation shield device 21 and the storage device are sufficiently thick, radially, to prevent the passage through the respective device by the radioisotopes emitted from the stent. Moreover, the first passage 17 is sufficiently long so that the length of the precompressed stent 11 may be substantially maintained centrally in the storage device 16 where the walls thereof are sufficiently thick to prevent penetration of the radioisotopes emanating from the stent.

Referring back to FIG. 1, the first passage 17 of the storage device preferably extends substantially linearly from an access opening 33 to the stent transfer opening 18 thereof. The stent transfer opening terminates at the proximal coupling end 20 which cooperates with the proboscis 31 of the radiation shield to axially align the stent transfer opening 18 with the distal opening 23. Upon proper alignment and coupling, the compressed stent 11 may be delivered and transferred into the second passage 22.

In the preferred embodiment, the proximal coupling end 20 provides a receiving port 35 formed and dimensioned for sliding receipt of the proboscis 31 therein during aligned coupling between the distal coupling end 25 and the proximal coupling end 20. This receiving port 35 is further defined by an extension portion 36 extending proximally which in effect deepens the receiving port for a more stable coupling with the proboscis 31. As viewed in FIG. 5, this extension portion 36 is preferably conical-shaped and tapers inwardly.

The tolerance between an interior wall 37 defining the receiving port 35 and an exterior wall 38 defining the exterior of the proboscis 31 is adjusted to enable sliding removal of the proboscis 31 from the receiving port once the stent is loaded in the deployment device 13. Moreover, the tolerance is configured and designed to provide accurate alignment between the stent transfer opening 18 and the distal opening 23 so that the compressed stent 11 may properly pass therebetween without damage thereto. Preferably, this tolerance is in the range of about 0.002" inches to about 0.005" inches per side which is sufficient to substantially prevent inadvertent locking therebetween, while still maintaining accurate alignment.

While the proboscis 31 and the receiving port 35 are cylindrical-shaped, it will be understood that the transverse peripheral dimension of the interior wall 37 and that of the mating exterior wall 38 may form other geometric shapes which enable sliding receipt therebetween without departing from the true sprit and nature of the present invention. These different shapes, however, are preferably matched to one another and will thus not enable relative rotation about the respective longitudinal axes thereof.

The proximal coupling end 20 of the storage device 16 further includes a nipple portion 40 extending into the receiving port 35 to define the stent transfer opening 18. This conical-shaped nipple portion 40 is adapted to extend into the distal opening 23 of the radiation shield device 21 when the proboscis 31 is fully received in the receiving port 35. Accordingly, the diameter or perimetric dimension of the distal opening 23 is sufficient to receive at least the tip of nipple portion 40 therein. The stent transfer opening 18 is therefore positioned in the inside the distal opening 23 of the proboscis for delivery of the compressed stent when the storage device 16 and the shield device 21 are coupled together in axial alignment.

To further promote stability between the storage device 16 and the radiation shield device 21, a secondary coupling 41 may be applied. As best viewed in FIG. 1, the secondary coupling 41 is preferably in the form of a sleeve or the like which cooperates with the respective peripheral surfaces of the storage device 16 and the shield device 21 to retain the relative aligned positions therebetween. Thus, transportation and storage of the stent loading apparatus 10 is substantially simplified, while simultaneously shielding physicians and other handlers from radiation exposure by the radioactive stent therein.

In the preferred embodiment, this sleeve or secondary coupling 41 is provided by a conventional shrink-wrap material which is shrunk substantially around the collective cylindrical periphery of the storage device 16 and the radiation shield device 21 as a single unit. During fabrication, and after the storage device 16 and the radiation shield are assembled together as a single unit, the shrink-wrap material 41 may be placed about the unitary periphery. Upon heating, the shrink-wrap material will shrink around the unitary periphery for stable coupling therebetween. Thus, once the stent is precompressed and placed in the first passage 17 of the storage device, the shrink-wrap may be applied. The collective stent loading apparatus 10 is then complete for transport, storage or usage. Other secondary coupling devices, of course, may be applied.

Figure 4:
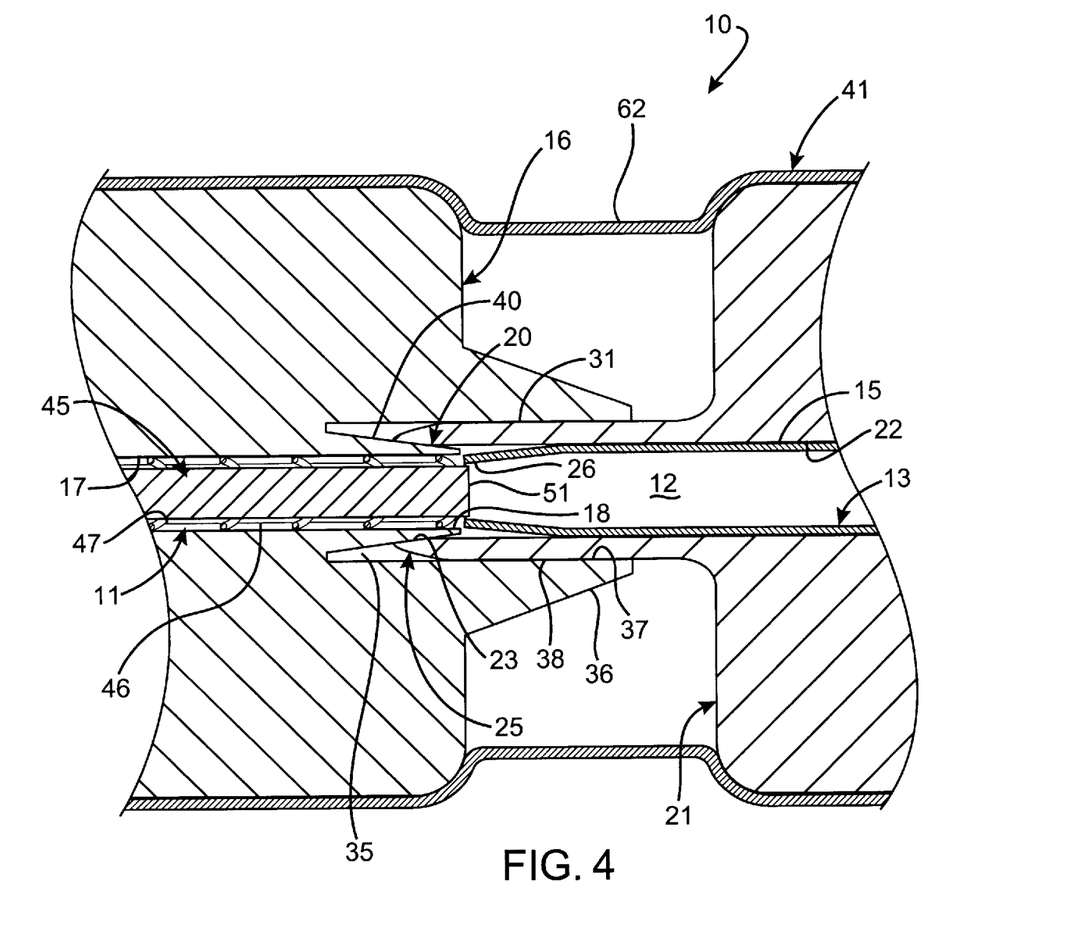
FIG. 4 is an enlarged, fragmentary, side elevation view, in cross-section, of the stent loading apparatus of FIG. 3A which illustrates the coupled engagement between the storage device and the radiation shield.

Referring now to FIG. 2, the stent loading apparatus 10 is shown coupled to an actuation device, generally designated 42, and the deployment device 13 before transfer of the compressed stent 11 is to commence. Initially, the deployment device 13 requires positioning in the radiation shield device 21 for receipt of the transferred stent 11. This is performed by first loosening the nut 30 of the Touhy-Borst fitting 27 by a sufficient amount to enable insertion of the deployment device therethrough. Subsequently, the distal end of the sheath 15 of the deployment device 12 is inserted through the deformable neck 32 and into the second passage 22. Advancement is to occur until the mouth portion 26 (i.e., the distal end) of sheath 15 is positioned substantially proximate to or even contacting the tip of the storage device nipple portion 40 (best viewed in FIG. 4). The nut 30 can then be tightened relative threaded portion 28 to secure the deployment device to the radiation shield device.

At the opposite end of the stent loading apparatus 10, the access opening 33 is configured for receipt of a contact end 43 of the actuation device 42. In the preferred embodiment, this actuation device 42 is selectively operated to urge the compressed stent 11 from the storage device 16 into the bore 12 of the deployment device sheath 15. Briefly, the actuation device 42, which will be described in greater detail below, includes a mandrel 45 formed for sliding receipt in the first passage 17 for abutting contact with an end of the compressed stent 11. To facilitate longitudinal alignment of the mandrel 45 with the storage device first passage 17, the contact end 43 of the actuation device 42 is adapted to extend into the access opening 33 of the storage device 16. As shown in FIG. 2, this contact end 43 is conical-shaped having a conical periphery which substantially matches the interior periphery of the inward taper of the access opening 33 into the first passage 17. Accordingly, the actuation device 42 may be secured to the stent loading apparatus 10 by a conventional pressfit, or through other coupling means such as a luer lock. Thus, upon press-fit insertion of the conical contact end 43 into the access opening 33, the mandrel 45 of the actuation device 42 will be axially aligned with the first passage 17 for sliding movement therein.

Figure 3A:
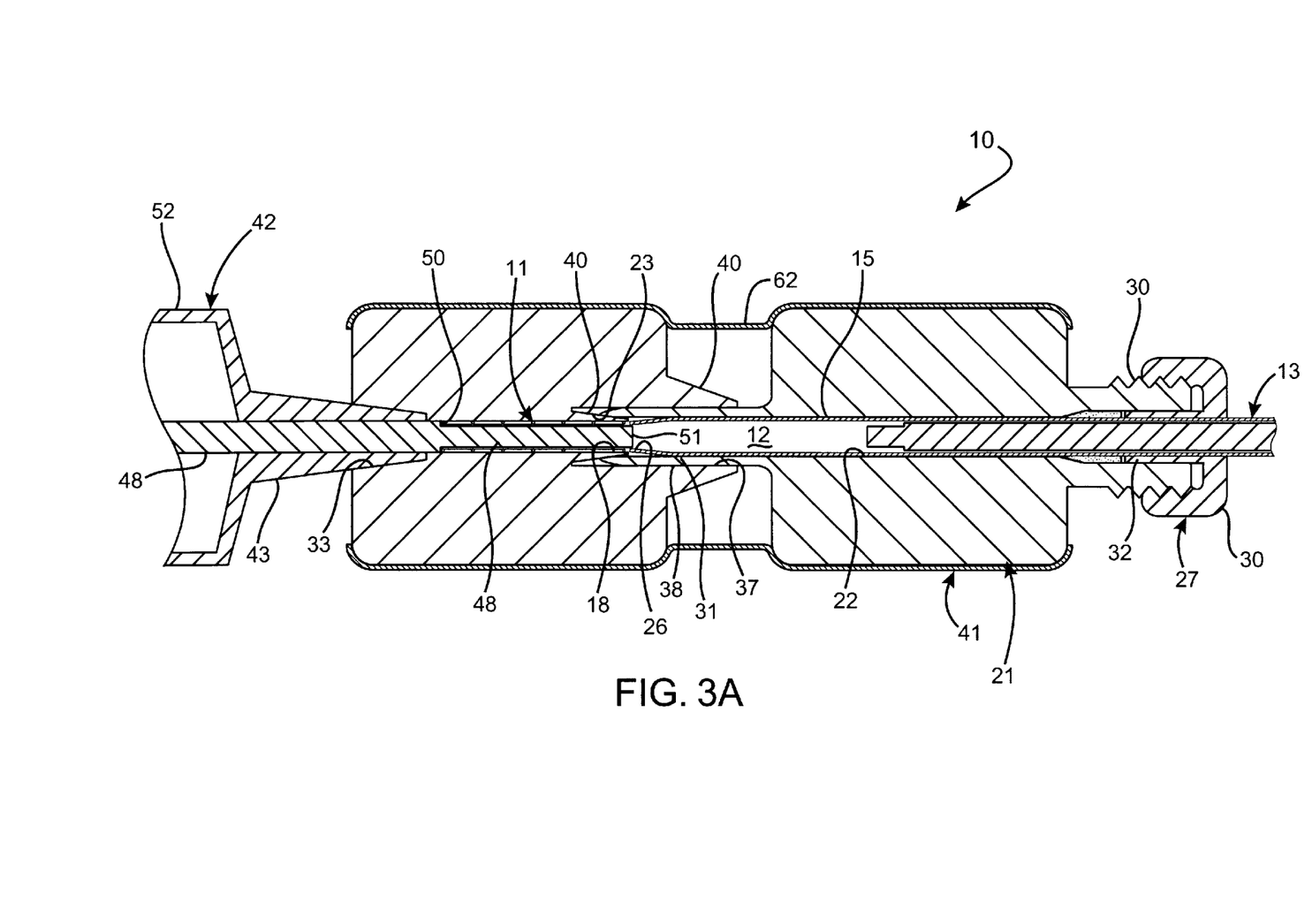
FIGS. 3A–3D is a series of fragmentary, side elevation views, in cross-section, of the stent loading apparatus of FIG. 2 illustrating loading of the radioactive stent from the first passage of the storage device to the second passage of the radiation shield and into the deployment device.

Once the stent loading apparatus 10, the actuation device 42 and the deployment catheter 13 are assembled as above-indicated, loading of the compressed stent may commence. Briefly, as best viewed in FIGS. 2 and 3A, the mandrel 45 of the actuation device 42 is selectively moved toward the compressed stent 11 for abutting contact thereagainst in the storage device 16. The mandrel 45 includes a distal support portion 46 sized to slideably extend into the lumen 47 of the prefolded or precompressed stent 11. The transverse cross-sectional dimension of the support portion 46 is preferably circular and is of a diameter sized to provided sufficient radial support to the precompressed stent 11 during transfer into the bore portion 12 of the deployment device 13, while enabling substantially unencumbered sliding receipt into the stent lumen 47. In the preferred embodiment, the diameter of the support portion is about 30% to about 99% of the diameter of the stent lumen 47 in the precompressed condition, and is more preferably about 80% of the diameter of the stent lumen 47.

The mandrel 45 further includes a pushrod portion 48 coupled to an opposite end of the support portion 46 which is formed and dimensioned for sliding receipt into the first passage 17 of the storage device 16. This pushrod portion 48 has a transverse cross-sectional dimension sized to slideably engage the interior walls of the first passage 17 in a manner axially aligning the support portion 46 with the stent lumen for insertion therein, while further being sized to slideably reciprocate for advancement and withdrawal from the stent loading apparatus.

As the mandrel 45 is further advanced to a first position (from FIG. 2 to FIG. 3A), the support portion 46 is advanced through the stent lumen 47 until a an annular shoulder 50 of the pushrod portion 48 abuts an end of the compressed stent to commence movement of the stent toward the second passage 22. Preferably, the length of the support portion 46 is at least as long as that of the stent in the compressed condition. More preferably, as best viewed in FIGS. 3A and 4, an insert end 51 of the support portion 46 is longitudinally configured to extend just past the proximal end of the stent 11 when mandrel distal shoulder 50 abuts the distal end of the compressed stent 11. As the radially supported stent 11 and the mandrel 45 are advanced toward the second passage 22 to a position proximate the stent transfer opening 18, as a unit, the insert end 51 protrudes into the mouth portion 26 of the bore 12 of the deployment device. The insert end 51, therefore, may taper inwardly or further be stepped to facilitate insertion into not only the mouth 26 of the sheath 15, but into the lumen 47 of the stent 11 as well.

Figure 3B:
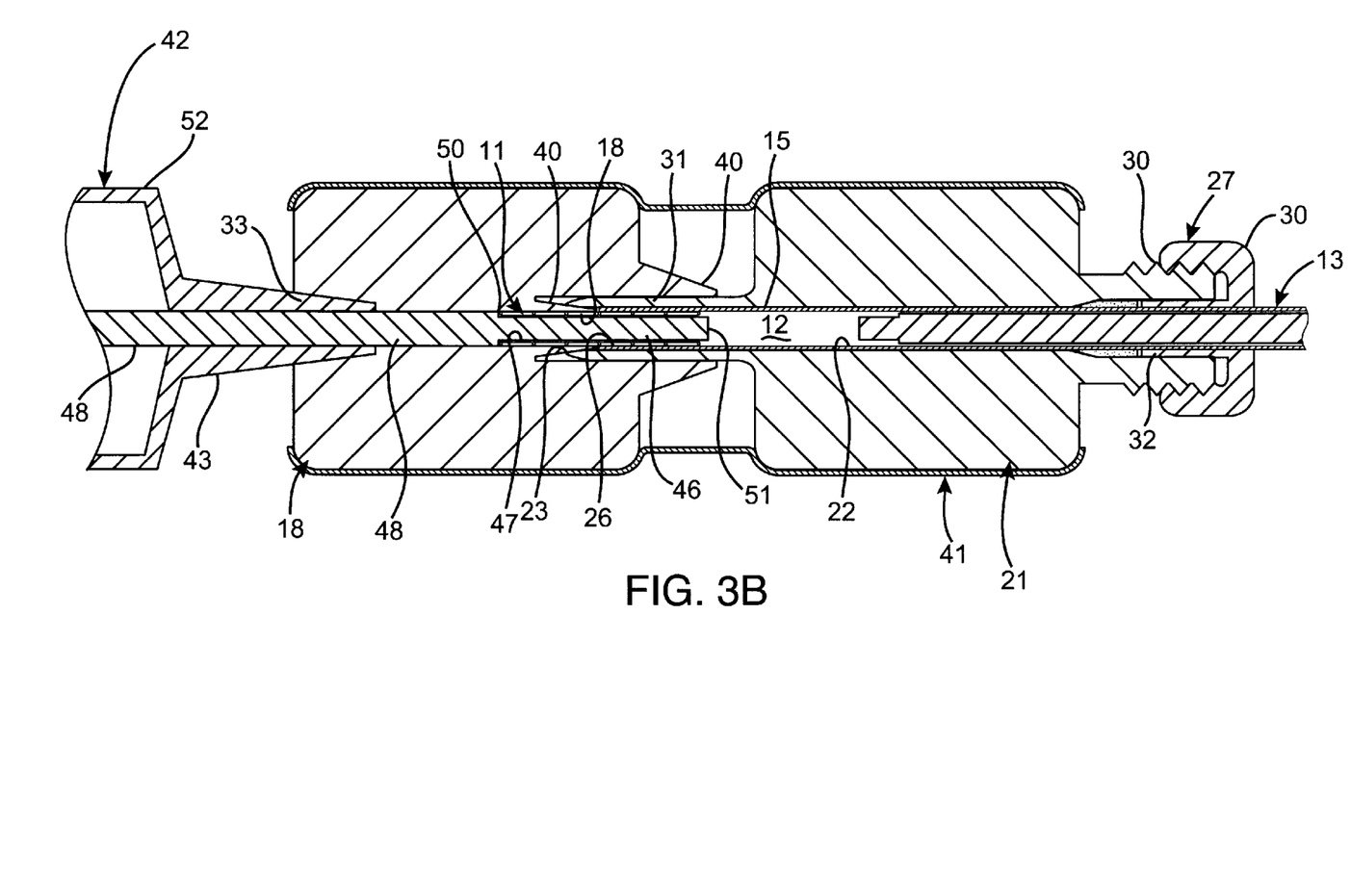

Accordingly, as the mandrel 45 is further advanced into the bore 12 of the deployment device 13, the shoulder 50 of the pushrod portion 48 moves the compressed stent past the mouth portion 26. As shown in FIG. 3B, the mouth portion 26 is sufficiently widened to receive the stent 11 and the support portion 46 as a unit. The stent, thus, cooperates with the support portion and the interior walls of the bore 12 to maintain the stent in the compressed condition during transfer. Once the mandrel 45 advances the support portion 46 and the mounted stent 11 fully into the bore 12 (FIG. 3C), the mandrel 45 is selectively retracted from the bore 12 in the opposite direction. During the withdrawal, the inward taper of the mouth portion 26 of the deployment device sheath 15 causes the compressed stent 11 to be removed from the support portion 46 for retainment in the bore 12 (FIG. 3D).

Figure 5:
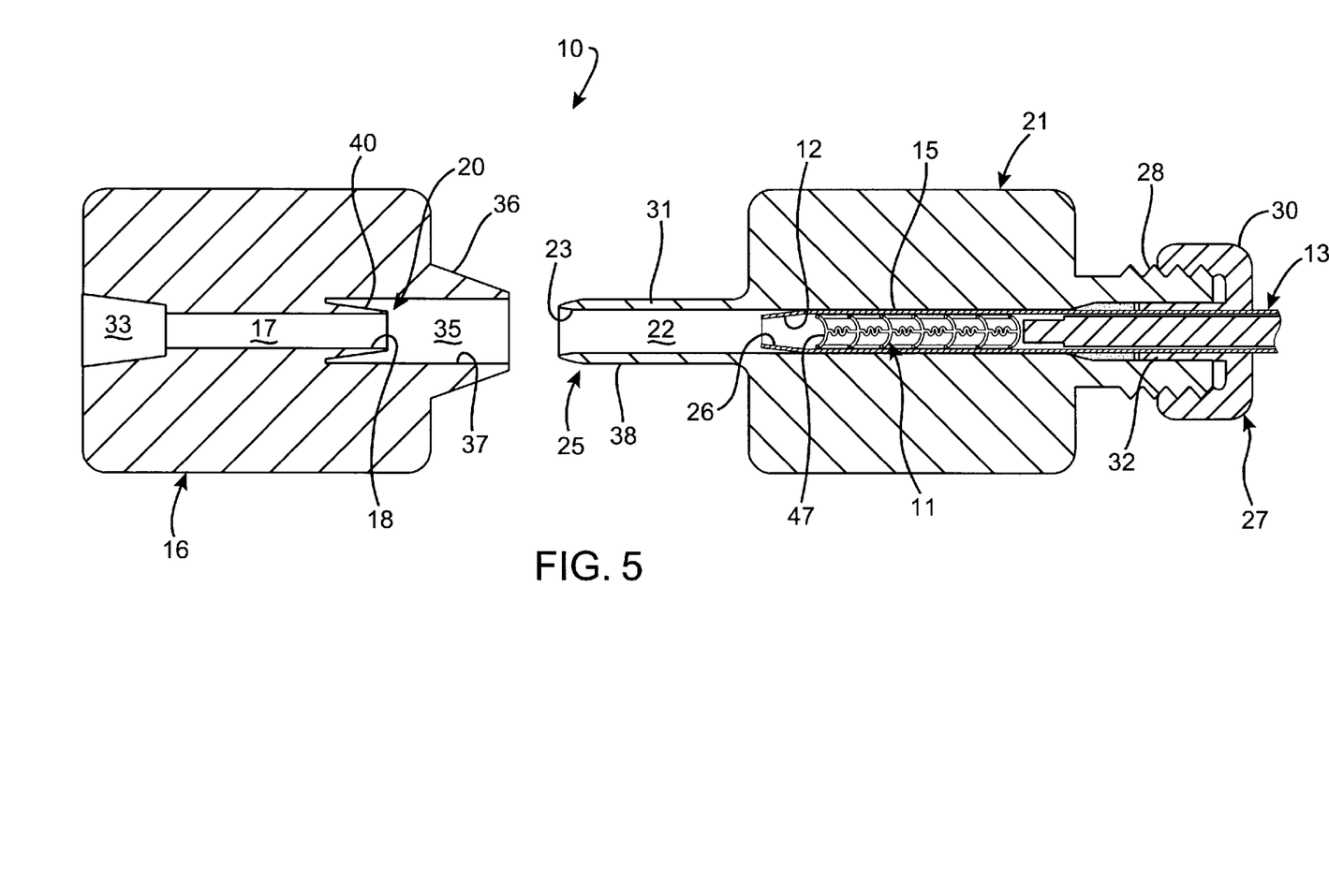
FIG. 5 is a fragmentary, side elevation view, in cross-section, of the stent loading apparatus of FIG. 1, and illustrating separation of the storage device from the radiation shield after loading of the stent into the deployment catheter.

Subsequently, the contact end 43 of the actuation device 42 may be removed from the access opening 33, and the nut 30 of the Touhy-Borst fitting 27 is loosened so that the deployment device 13 can be further retracted into the shield device 21 (FIG. 5). The shrink-wrap material is then cut or torn away. For example, the shrink-wrap material may be perforated (not shown) to facilitate tearing. After the shrink-wrap material 41 is separated from the stent loading apparatus 10, the storage device 16 may be removed from the shield device 21. The shield device 21 and the deployment device 13 are then ready for operable use, as disclosed in U.S. Pat. No. 5,605,530.

Figure 6:
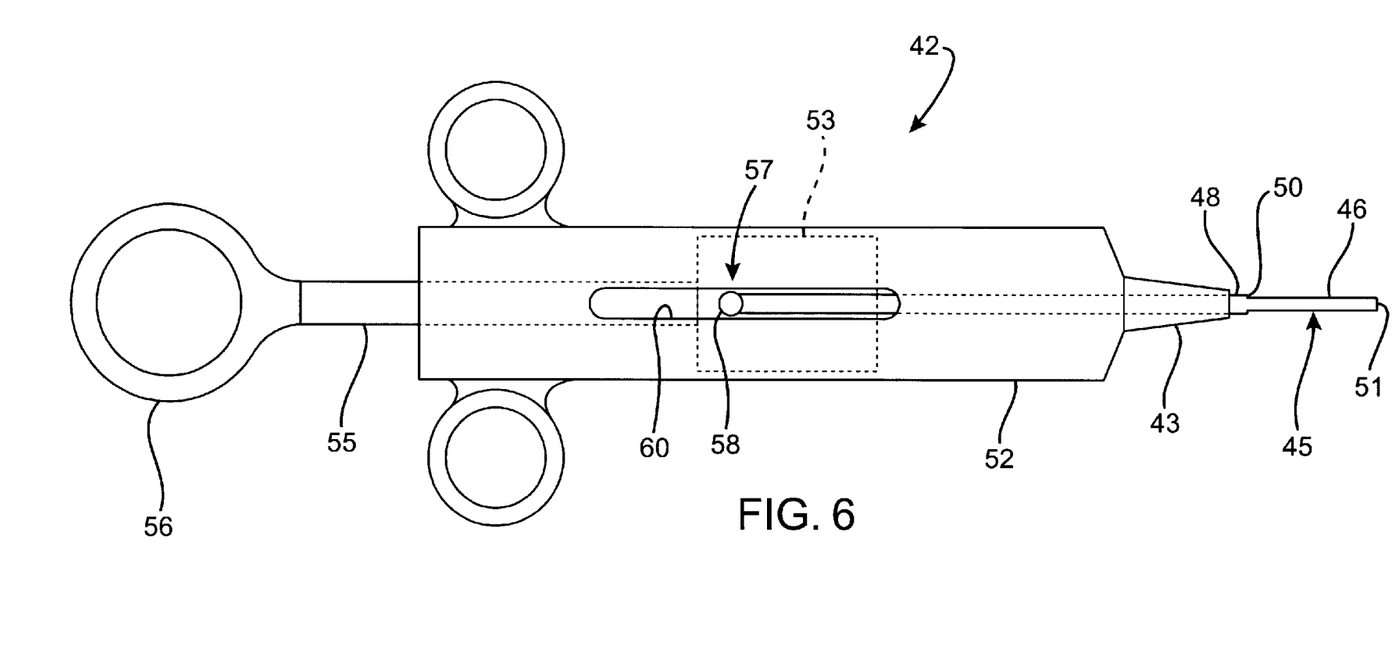
FIG. 6 is a fragmentary, side elevation view of the actuation device employed to urge the compressed stent from the storage device to the radiation shield device.

In accordance with the present invention, the actuation device 42 is provided by a syringe-type mechanism (FIG. 6) having a body portion 52 terminating at the contact end 43. A loading plunger 53 is coupled to the mandrel 45 which cooperates with the body portion 52 to control and align the mandrel during movement between the first position and an extended second position. A shaft portion 55 is coupled to the loading plunger 53 which in turn is coupled to a handle 56 for control of the mandrel 45. In the preferred embodiment, a stop member 57 may be included which limits the travel of the mandrel into bore 12. For example, the stop member 57 may be provided by a knob 58 or the like which extend outwardly from the loading plunger 53 or mandrel 45. In this arrangement, the knob 58 is adapted to reciprocate longitudinally along a slot 60 formed in the body portion 52 of the actuation device 42, until the knob 58 contacts one of the ends of the slot 60.

Figure 7:
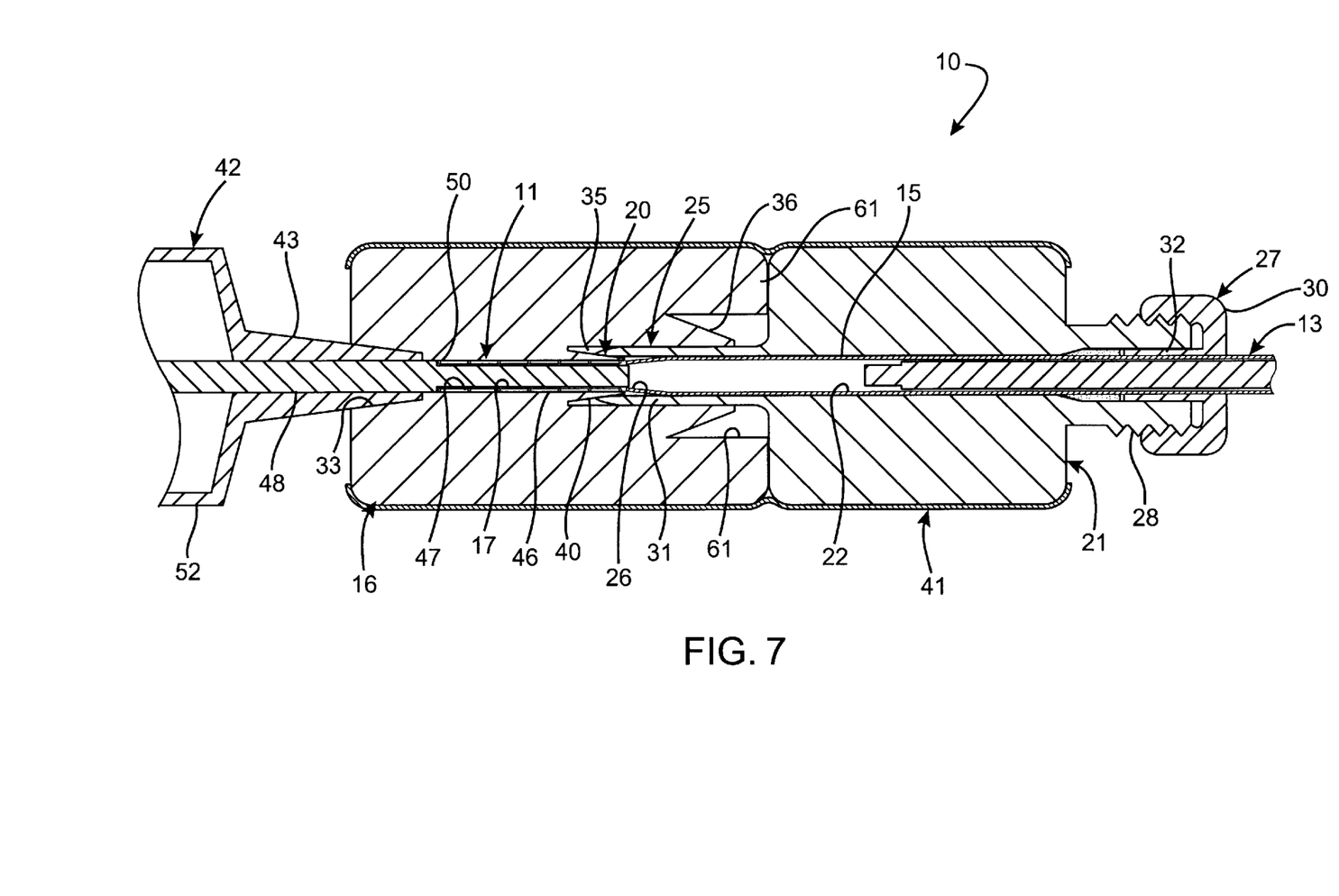
FIG. 7 is a fragmentary, side elevation view, in cross-section, of an alternative embodiment of the stent loading apparatus of FIG. 1.

Referring now to FIG. 7, an alternative embodiment stent loading apparatus 10 is represented wherein an annular ring portion 61 is included to promote stability when distal coupling end 25 of the shield device 21 is coupled to the proximal coupling end 20 of the storage device 16. Accordingly, this concept, in combination with the shrink-wrap material 41, reduces potential failure or fracture of the proboscis 31 of the radiation shield device 21 while inserted in the receiving port 35 of the storage device 16 when lateral forces are applied to the stent loading apparatus 10.

The annular ring portion 61 is preferably integrally formed with the storage device 16, and protrudes longitudinally from the proximal end thereof in a direction toward the shield device 21. This ring portion 61 further preferably extends past the extension portion 36 to a position proximate to, if not contacting, the distal face (as shown in FIG. 7) of the radiation shield device 21. Thus, the annular unsupported portion 62 of the shrink-wrap material 41 of the embodiment of FIG. 1 is substantially reduced to further promote stability.

In another aspect and as apparent from the description of the present invention, a method is provided for loading a self-expanding stent 11, in a compressed condition, into a bore portion 12 of a deployment device 13. The method includes: A) inserting the stent 11 longitudinally into an elongated first passage 17 of a storage device 16 configured for sliding receipt of the stent 11 therein in the compressed condition; and B) releasably coupling a shield device 21 to the storage device 16 in a manner aligning a distal opening 23 of an elongated second passage 22 extending through the shield device 21 with a stent transfer opening 18 of the first passage 17 of the storage device 16 (FIG. 1). The method further includes C) positioning the deployment device 13 in the elongated second passage 22 such that a mouth portion 26 into bore portion 12 of the deployment device 13 is positioned proximate the distal opening 23 of the second passage 22 (FIGS. 3A and 4); and D) urging the compressed stent 11 in the first passage 17 of the storage device 16 from the stent transfer opening 18 through the distal opening 23 into the second passage 22, and into the mouth portion 26 of the bore portion 12 for retainment therein in the compressed condition (FIGS. 3B and 3C).

Preferably, the releasably coupling event further includes placing an elongated proboscis 31, defining the distal opening 23 of the shield device 21, into a receiving port 35 of the storage device 16 for aligned communication between the stent transfer opening 18 and the distal opening 23 into the second passage 22. This event further includes placing a nipple portion 40 of the stent transfer opening 18 into the distal opening 23 of the proboscis 31 during the aligned coupling such that the stent transfer opening 18 of the storage device 16 is positioned inside the distal opening 23 of the radiation shield device 21.

The urging event D) may further include passing a mandrel 45 through an access opening 33 of the first passage 17 of the storage device 16 to contact an end of the compressed stent 11 for sliding movement toward the distal opening 23 of the radiation shield device 21 and into the bore portion 12 of the deployment device 13. This event may further include inserting a support portion 46 of the mandrel 45 into the compressed stent 11, while maintained in the storage device first passage 17, to provide compressive radial support thereof.

Figure 3C:
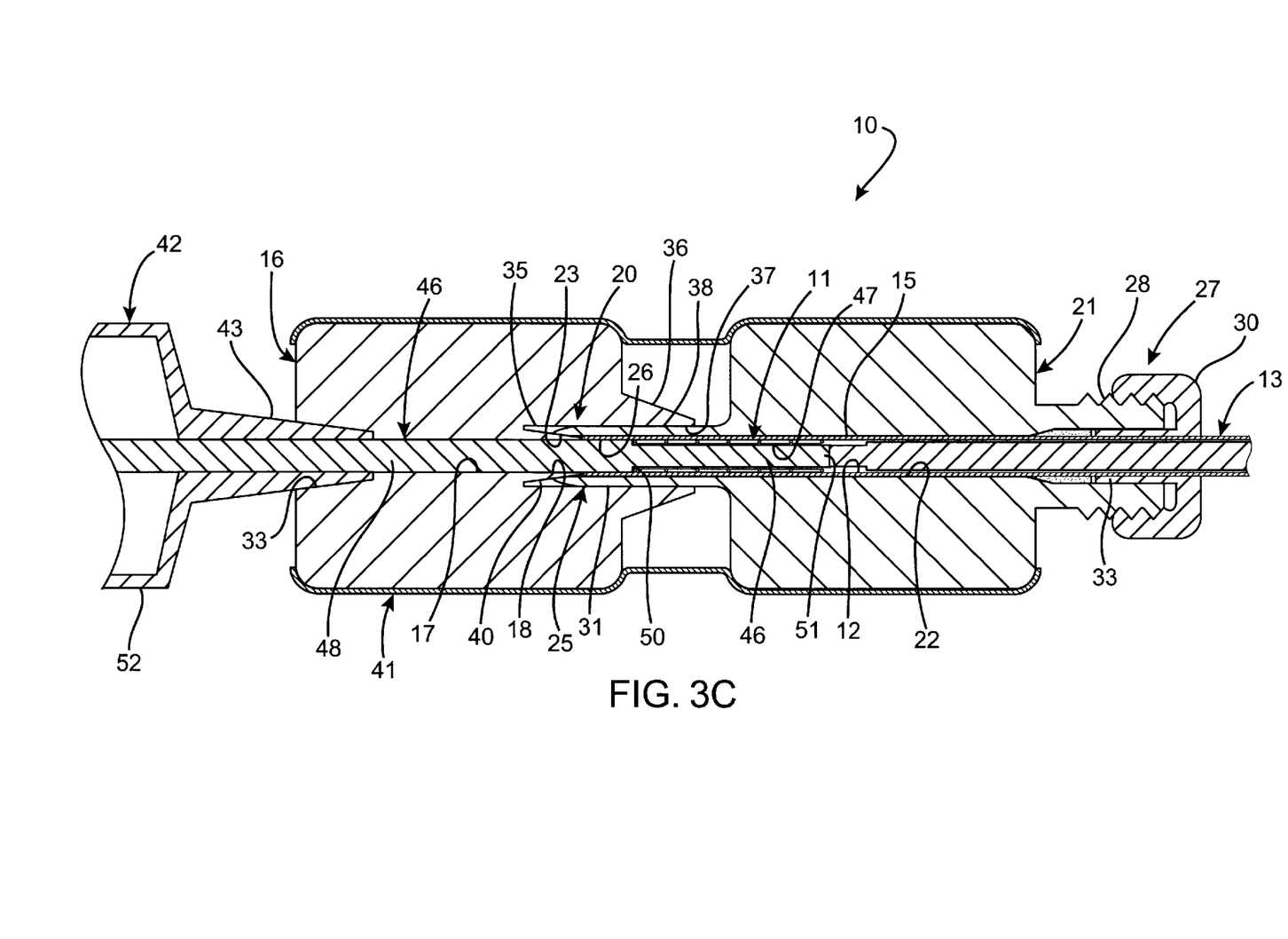
Figure 3D:
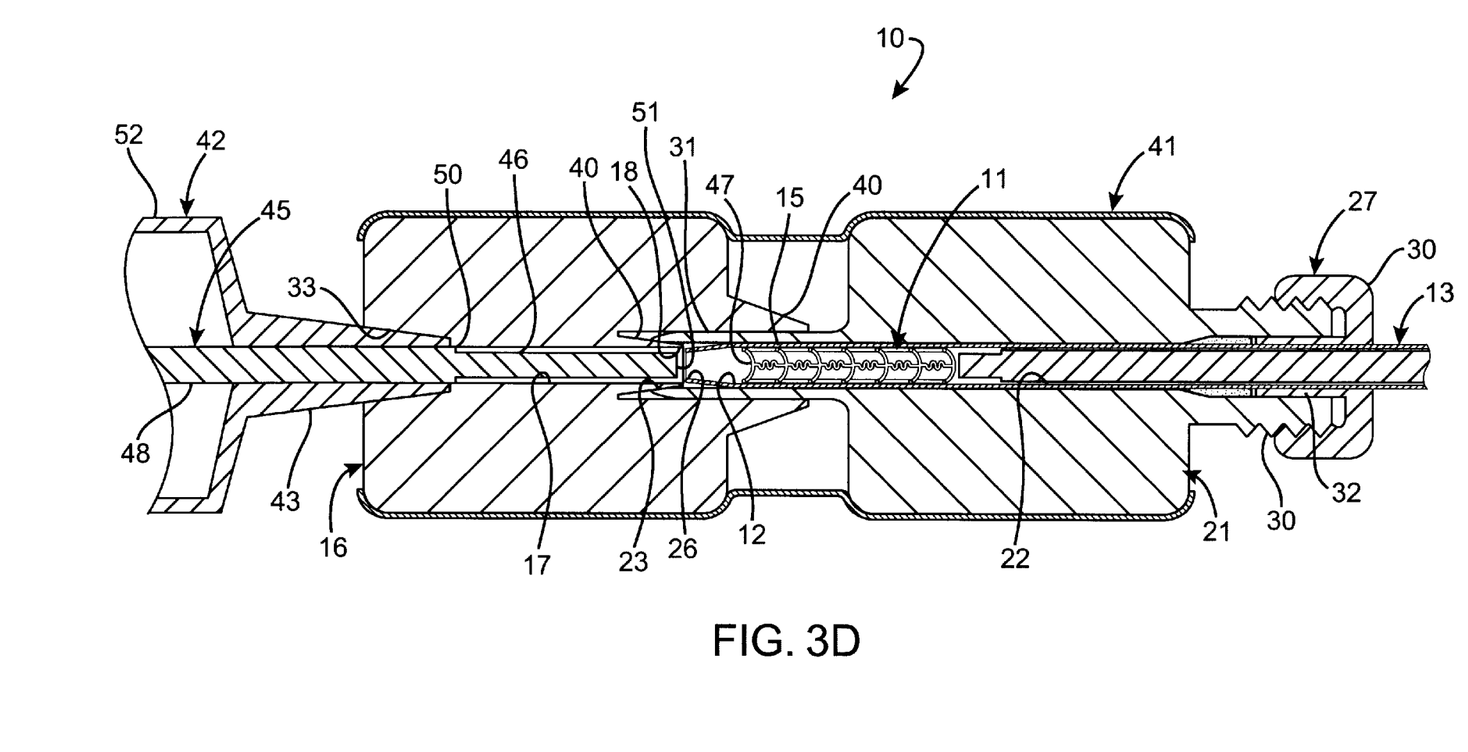

In the preferred method of the present invention, the urging event further includes actuating the mandrel 45 to selectively move the mandrel 45 to a first position (FIG. 3A) and a second position (FIG. 3C). In the first position, the support portion of the mandrel 45 is inserted into the compressed stent 11 while the stent is maintained in the storage device first passage 17, while in the second position, the support portion 46 and the compressed stent 11 are simultaneously urged, as a unit, into the bore portion 12 of the deployment device 13 in the shield device 21. Subsequently, the urging the support portion event further includes passing mandrel 45 into the second passage 22 of the shield device 21 through the distal opening 23 thereof.

After the urging event, the method of the present invention includes separating the storage device 16 from the shield device 21 (FIG. 5). The radiation shield and the enclosed stent and deployment device 13 are then ready for operable use.

Finally the actuating event of the urging event further includes limiting passage of the mandrel 45 into the second passage 22 toward the second position through a stop member 57.

The releasably coupling event B) further includes placing an elongated proboscis 31 into a receiving port 35 of the storage device 16 for aligned communication between the stent transfer opening 18 and the distal opening 23 into the second passage 22.

As above indicated, to further promote stability, the method of the present invention further includes the event of shrink-wrapping a shrink-wrap material 41 substantially around the collective periphery of the storage device 16 and the shield device 21. After the urging the compressed stent event, the method includes removing the shrink-wrap material 41 to enable separation of the storage device 16 from the shield device 21.

What is claimed is:

1. A stent loading apparatus for loading a self-expanding radioactive stent into a bore portion of a deployment device configured for sliding receipt and retainment of the radioactive stent therein in a compressed condition, said loading apparatus comprising:
   a storage device defining an elongated first passage formed and dimensioned for sliding receipt of the radioactive stent in the compressed condition, said first passage terminating at a stent transfer opening of a proximal coupling end of said storage device; and
   a radiation shield defining an elongated second passage terminating at a distal opening of a distal coupling end thereof, the radiation shield distal coupling end and the storage device proximal coupling end cooperate to align the distal opening of the radiation shield in receiving communication with the stent transfer opening of the storage device, and said second passage being formed and dimensioned for receipt of said deployment device therein in a manner positioning a mouth portion of the deployment device bore portion substantially adjacent the stent transfer opening of the storage device such that upon urging of the radioactive stent in a direction toward the radiation shield, the radioactive stent may be slideably transferred from the first passage and into the mouth portion of the bore portion for retainment therein in the compressed condition.

2. The stent loading apparatus according to claim 1 wherein,
   the radiation shield distal coupling end and the storage device proximal coupling end cooperate to axially align the distal opening of the radiation shield with the stent transfer opening of the storage device.

3. The stent loading apparatus according to claim 2 wherein,
   the first passage and the second passage are co-axially aligned.

4. The stent loading apparatus according to claim 1 wherein,
   the radiation shield distal coupling end includes an elongated proboscis defining said distal opening and upon which the second passage extends longitudinally therethrough, and
   said storage device proximal end defines a receiving port formed and dimensioned for sliding receipt of the proboscis therein during aligned coupling between the distal coupling end and the proximal coupling end.

5. The stent loading apparatus according to claim 4 wherein,
   the stent transfer opening of the storage device first passage further terminates at a nipple portion tapering inwardly and extending into said receiving port, said nipple portion having a proximal end thereof adapted to extend into the distal opening of the proboscis during said aligned coupling such that said stent transfer opening of the storage device is positioned inside said distal opening of the radiation shield.

6. The stent loading apparatus according to claim 5 wherein,
   the nipple portion is further adapted to abut the distal end of the deployment device when said deployment device is fully received in the second passage.

7. The stent loading apparatus according to claim 6 further including:
   a secondary coupling device stably coupling the storage device and the radiation shield together.

8. The stent loading apparatus according to claim 7 wherein,
   said secondary coupling device includes a shrink-wrap material shrunk substantially around the collective periphery of the storage device and the radiation shield.

9. The stent loading apparatus according to claim 1 further including:
   a secondary coupling device stably coupling the storage device and the radiation shield together.

10. The stent loading apparatus according to claim 9 wherein,
    said secondary coupling device includes a shrink-wrap material shrunk substantially around the collective periphery of the storage device and the radiation shield.

11. The stent loading apparatus according to claim 1 wherein,
    said storage device is sufficiently thick to substantially prevent penetration of radioactive particles out of the storage device which are emitted from the radioactive stent contained in the first passage.

12. The stent loading apparatus according to claim 11 wherein, said storage device is composed of a polycarbonate.

13. A stent loading apparatus for loading a self-expanding stent into a bore portion of a deployment device configured for sliding receipt and retainment of the stent therein in a compressed condition, said loading apparatus comprising:
   a storage device defining an elongated first passage formed and dimensioned for sliding receipt of the stent in the compressed condition, said first passage extending longitudinally through the storage device from an access opening to an opposite stent transfer opening;
   a shield device providing an elongated second passage terminating at a distal opening, said second passage being formed and dimensioned for receipt of said deployment device therein in a manner positioning a mouth portion of the deployment device bore portion proximate the distal opening of the second passage;
   a coupling device releasably coupling the shield device to the storage device to align the distal opening of the shield device in receiving communication with the stent transfer opening of the storage device; and
   an elongated mandrel configured to slideably extend through said access opening into said first passage and into abutting contact with the stent in the compressed condition to urge the stent from the first passage of the storage device to the second passage of the shield device and into the mouth portion of the bore portion for retainment therein in the compressed condition.

14. The stent loading apparatus according to claim 13 wherein,
   said mandrel includes a pushrod having a distal shoulder portion adapted to abut a distal end of the compressed stent, and a support portion extending from said shoulder portion of the pushrod and into the compressed stent in the compressed condition for radial support during transfer from the first passage and into the bore portion of the deployment device.

15. The stent loading apparatus according to claim 14 wherein,
   the diameter of said support portion sized for sliding receipt thereof in the inner diameter of the stent while in the compressed condition.

16. The stent loading apparatus according to claim 14 wherein,
   an insert end of said support portion is adapted to extend past the proximal end of said stent when mandrel distal shoulder portion abuts the distal end of the compressed stent.

17. The stent loading apparatus according to claim 16 wherein,
   said insert end of said support portion is adapted to extend into said mouth portion of the bore portion of the deployment device during transfer of the compressed stent into the bore portion of the deployment device.

18. The stent loading apparatus according to claim 16 further including:
   an actuation device coupled to said mandrel for selective movement between a first position, placing the support portion of the mandrel in the stent in said storage device, and a second position, urging the support portion and the compressed stent simultaneously as a unit into the bore portion of the deployment device in said shield device.

19. The stent loading apparatus according to claim 18 wherein,
   said actuation device includes a contact end adapted to extend into the access opening of the storage device to enable aligned movement of the mandrel to the first position.

20. The stent loading apparatus according to claim 19 wherein,
   said contact end is tapered inwardly and adapted to be press-fit into the access opening of the storage device.

21. The stent loading apparatus according to claim 18 wherein,
   said actuation device further includes a stop member configured to limit the movement of the mandrel toward the second position.

22. The stent loading apparatus according to claim 13 wherein,
   the coupling device includes a first coupling at a proximal end of said storage device and a second coupling at a distal end of the shield device, the first coupling and the second coupling cooperating to axially align the distal opening of the shield device with the stent transfer opening of the storage device.

23. The stent loading apparatus according to claim 22 wherein,
   the second coupling includes an elongated proboscis at the shield device distal end defining the distal opening of the shield device upon which the second passage extends longitudinally therethrough, and
   said first coupling defines a receiving port at the storage device proximal end formed and dimensioned for sliding receipt of the proboscis therein during aligned coupling between the first coupling and the second coupling.

24. The stent loading apparatus according to claim 23 wherein,
   the stent transfer opening to the first passage of the storage device further terminates at a nipple portion tapering inwardly and extending into said receiving port, said nipple portion having a proximal end thereof adapted to extend into the distal opening of the proboscis during said aligned coupling such that said stent transfer opening of the storage device is positioned inside said distal opening of the shield device.

25. The stent loading apparatus according to claim 24 wherein,
   the nipple portion is further adapted to abut the distal end of the deployment device when said deployment device is fully received in the second passage.

26. The stent loading apparatus according to claim 25 further including:
   a shrink-wrap material shrunk substantially around the collective periphery of the storage device and the shield device.

27. The stent loading apparatus according to claim 13 further including:
   a shrink-wrap material shrunk substantially around the collective periphery of the storage device and the shield device.

28. The stent loading apparatus according to claim 13 wherein,
   said stent is a radioactive stent adapted to emit radiation radially therefrom, and
   said storage device and said shield device are sufficiently thick to substantially prevent penetration of the radiation out of the respective storage device and the shield device which are emitted from the radioactive stent contained in one of the first passage and the second passage, respectively.

29. A method of loading a self-expanding stent, in a compressed condition, into a bore portion of a deployment device configured for sliding receipt and retainment of the compressed stent therein, said method comprising:

inserting the stent longitudinally into an elongated first passage of a storage device configured for sliding receipt of the stent therein in the compressed condition;

releasably coupling a shield device to the storage device in a manner aligning a distal opening of an elongated second passage extending through the shield device with a stent transfer opening of the first passage of the storage device; positioning the deployment device in the elongated second passage such that a mouth portion into bore portion of the deployment device is positioned proximate the distal opening of the second passage; and urging the compressed stent in the first passage of the storage device from the stent transfer opening through the distal opening into the second passage, and into the mouth portion of the bore portion for retainment therein in the compressed condition.

30. The method according to claim 29 wherein, said releasably coupling further includes placing an elongated proboscis, defining the distal opening of the shield device, into a receiving port of the storage device for aligned communication between the stent transfer opening and the distal opening into the second passage.

31. The method according to claim 30 wherein, said placing an elongated proboscis further includes placing a nipple portion of the stent transfer opening, extending into said receiving port, into the distal opening of the proboscis during said aligned coupling such that said stent transfer opening of the storage device is positioned inside said distal opening of the radiation shield.

32. The method according to claim 29 wherein, said urging further includes passing a mandrel through an access opening of the first passage of the storage device to contact an end of the compressed stent for sliding movement toward the distal opening of the radiation shield and into the bore portion of the deployment device.

33. The method according to claim 32 wherein, said urging further includes inserting a support portion of the mandrel into the compressed stent while maintained in the storage device first passage to provide compressive radial support thereof.

34. The method according to claim 32 wherein, said urging further includes actuating the mandrel to selectively move the mandrel to a first position, inserting a support portion of the mandrel into the compressed stent while maintained in the storage device first passage, and a second position, urging the support portion and the compressed stent simultaneously as a unit into the bore portion of the deployment device in said shield device.

35. The method according to claim 34 wherein, said urging the support portion further includes passing mandrel into the second passage of the shield device through the distal opening thereof.

36. The method according to claim 35 wherein, said actuating further includes limiting passage of the mandrel into the second passage toward the second position through a stop member.

37. The method according to claim 30 further including:

shrink-wrapping a shrink-wrap material substantially around the collective periphery of the storage device and the shield device to further couple the storage device and the shield device together.

38. The method according to claim 34 wherein, said releasably coupling further includes placing an elongated proboscis, defining the distal opening of the shield device, into a receiving port of the storage device for aligned communication between the stent transfer opening and the distal opening into the second passage.

39. The method according to claim 38 further including:

shrink-wrapping a shrink-wrap material substantially around the collective periphery of the storage device and the shield device to further couple the storage device and the shield device together.

40. The method according to claim 38 further including:

after urging the compressed stent, removing the shrink-wrap material to enable separation of the storage device from the shield device.

41. The method according to claim 29 wherein, said releasably coupling is performed by shrink-wrapping a shrink-wrap material shrunk substantially around the collective periphery of the storage device and the shield device.

42. The method according to claim 29 further including:

after urging, separating the storage device from the shield device.

* * * * *